(12) United States Patent
Mavliev (10) Patent No.: US 7,738,101 B2
(45) Date of Patent: Jun. 15, 2010

(54) SYSTEMS AND METHODS FOR IN-LINE MONITORING OF PARTICLES IN OPAQUE FLOWS

(76) Inventor: Rashid Mavliev, 357 W. Rincon Ave., Unit C, Campbell, CA (US) 95008

( * ) Notice: Subject to any disclaimer, the term of this patent is extended or adjusted under 35 U.S.C. 154(b) by 143 days.

(21) Appl. No.: 12/169,500

(22) Filed: Jul. 8, 2008

(65) Prior Publication Data
US 2010/0007879 A1    Jan. 14, 2010

(51) Int. Cl.
*G01N 15/02*    (2006.01)
*G01N 33/36*    (2006.01)

(52) U.S. Cl. .................. 356/336; 356/246
(58) Field of Classification Search ......... 356/335–343, 356/244–246, 436, 440
See application file for complete search history.

(56) References Cited

U.S. PATENT DOCUMENTS

| | | | |
|---|---|---|---|
| 3,873,203 A | 3/1975 | Friedman et al. |
| 4,983,038 A | 1/1991 | Ohki et al. |
| 5,007,732 A | 4/1991 | Ohki et al. |
| 5,125,737 A | 6/1992 | Rodriguez et al. |
| 5,159,403 A | 10/1992 | Kosaka |
| 5,311,290 A | 5/1994 | Olson et al. |
| 5,414,508 A | 5/1995 | Takahashi et al. |
| 5,521,699 A | 5/1996 | Kosaka et al. |
| 5,548,395 A | 8/1996 | Kosaka |
| 5,650,847 A | 7/1997 | Maltsev et al. |
| 5,663,503 A | 9/1997 | Dam et al. |
| 5,690,895 A | 11/1997 | Matsumoto et al. |
| 5,710,069 A | 1/1998 | Farkas et al. |
| 5,721,433 A | 2/1998 | Kosaka et al. |
| 5,739,902 A | 4/1998 | Gjelsnes et al. |
| 5,818,583 A | 10/1998 | Sevick-Muraca et al. |
| 5,824,269 A | 10/1998 | Kosaka et al. |
| 5,835,211 A | 11/1998 | Wells et al. |
| 5,880,835 A | 3/1999 | Yamazaki et al. |
| 5,948,684 A | 9/1999 | Weigl et al. |
| 5,972,710 A | 10/1999 | Weigl et al. |
| 6,109,119 A | 8/2000 | Jiang et al. |

(Continued)

OTHER PUBLICATIONS

Mavliev, R., 1992 Optical Determination of Size and Concentration of Particles below 100 nm: Method and Applications, In: Nucleation and Atmospheric Aerosols. Eds.: Fukuta, Wagner, A. Deepak Publishing, Hampton, VI, USA, 377-380.

(Continued)

*Primary Examiner*—Hoa Q Pham
(74) *Attorney, Agent, or Firm*—Buchanan Ingersoll & Rooney PC (57) ABSTRACT

Systems and methods are disclosed for particle monitoring. An exemplary method includes confining a flowable sample which is opaque to at least a first range of wavelengths of light waves; measuring transparency of the flowable sample; compressing the flowable sample in a first direction while confining the sample in a second direction parallel to a flow direction of the flowable sample and orthogonal to the first direction, while elongating the sample in a third direction orthogonal to the first and second directions. When the sample is compressed in the first direction, the sample becomes transparent to at least one of the wavelengths in the first range of wavelengths, and the method can include identifying characteristics of particles contained in the sample which has been compressed.

26 Claims, 12 Drawing Sheets

U.S. PATENT DOCUMENTS

| | | | |
|---|---|---|---|
| 6,136,272 | A | 10/2000 | Weigl et al. |
| 6,159,739 | A | 12/2000 | Weigl et al. |
| 6,211,956 | B1 | 4/2001 | Nicoli |
| 6,246,474 | B1 | 6/2001 | Cerni et al. |
| 6,710,874 | B2 | 3/2004 | Mavliev |
| 7,294,249 | B2 | 11/2007 | Gawad et al. |
| 7,318,902 | B2 | 1/2008 | Oakey et al. |
| 2009/0051912 | A1* | 2/2009 | Salazar et al. ............... 356/246 |

OTHER PUBLICATIONS

V. P. Maltsev, 2000, Scanning flow cytometry for individual particle analysis, Review of Scientific Instruments, 71:243-255.

A. J. Adorjan, et al., Particle sizing in strongly turbid suspensions with the one-beam cross-correlation dynamic light-scattering technique. Applied Optics, 1999, 38:3409-3416.

N. L. Swanson, B. D. Billard, and T. L. Gennaro, Limits of optical transmission measurements with application to particle sizing techniques. Applied Optics, 1999, 38:5887-5893.

H. Schnablegger and O. Glatter, Sizing of colloidal particles with light scattering: correction for beginning multiple scattering. Applied Optics, 1995, 34:3489-3501.

A. P. Nefedov et al., Application of a forward-angle-scattering transmissometer for simultaneous measurements of particle size and number density in an optically dense medium. Applied Optics, 1998, 37:1682-1689.

* cited by examiner

SYSTEMS AND METHODS FOR IN-LINE MONITORING OF PARTICLES IN OPAQUE FLOWS

BACKGROUND

1. Field

The subject matter presented herein relates generally to the field of monitoring particles in a flowable sample, such as a slurry, emulsion or suspension.

2. Background Information

Liquid systems with high particulate concentrations are known. Examples of such systems are slurries used in chemical mechanical planarization (CMP) processes for the semiconductor industry and emulsions used in the pharmaceutical industry.

Optical methods of detection and characterization have been used for monitoring particle parameters in gas and liquid media. U.S. Pat. No. 6,710,874 to Mavliev discloses an apparatus and method for the optical characterization of particles in highly concentrated systems and is hereby incorporated by reference in its entirety.

SUMMARY

A particle monitoring system comprises a cuvette configured to confine a flowable sample, the flowable sample being opaque to at least a first range of wavelengths of light waves; a transparent flow compression element located within the cuvette and configured to compress the flowable sample in a first direction while controlling the sample in a second direction parallel to the direction of flow and orthogonal to the first direction while elongating the sample in a third direction orthogonal to the first and second directions, wherein when the sample is compressed in the first direction it becomes transparent to at least one of the wavelengths in the range of wavelengths of light waves; and a monitor for monitoring the flowable sample using the at least one wavelength.

A method of particle monitoring comprises confining a flowable sample, the flowable sample being opaque to at least a first range of wavelengths of light waves; measuring transparency of the flowable sample; compressing the flowable sample in a first direction while confining the sample in a second direction parallel to a flow direction of the flowable sample and orthogonal to the first direction, while elongating the sample in a third direction orthogonal to the first and second directions, wherein when the sample is compressed in the first direction, the sample becomes transparent to at least one of the wavelengths in the first range of wavelengths; and identifying characteristics of particles contained in the sample which has been compressed.

BRIEF DESCRIPTION OF THE DRAWINGS

As will be realized, different embodiments are possible, and the details disclosed herein are capable of modification in various respects, all without departing from the scope of the claims. Accordingly, the drawings and descriptions are to be regarded as illustrative in nature and not as restrictive. Like reference numerals have been used to designate like elements.

DETAILED DESCRIPTION

FIGS. 1A, 1B, 1C and 1D are provided as an introductory overview of the subject matter presented herein. In the exemplary particle monitoring system shown FIG. 1A, the sample flow Q with inclusions or particles 10 to be detected (represented as dots) can have converging and diverging parts. Arrows 20 represent light beam penetration depth that depends on optical properties of the sample, e.g., sample turbidity. A goal can be to provide light penetration in the narrowest part of the flow (1). In that case, an optical technique, such as dynamic light scattering 30, light extinction 40, light scattering 50, or a combination of techniques, can be used to detect impurities (e.g., particles, inclusions and so forth) in the flow, and/or to characterize the flow based on parameters such as particle count per unit volume.

Figure 1A:
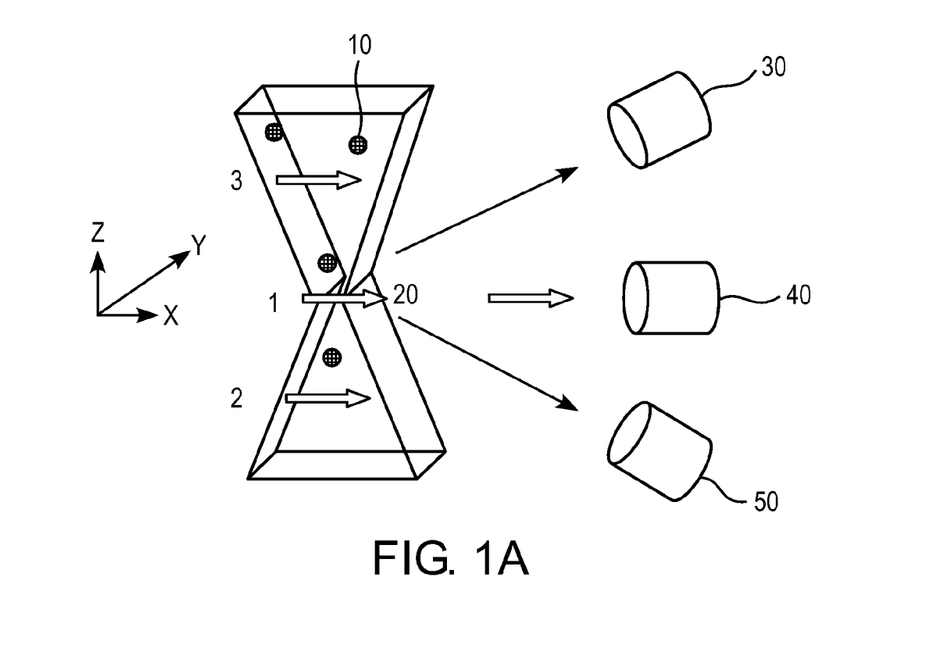
FIG. 1A shows an overview of flow in an exemplary embodiment of a particle monitoring system.
Figure 1B:
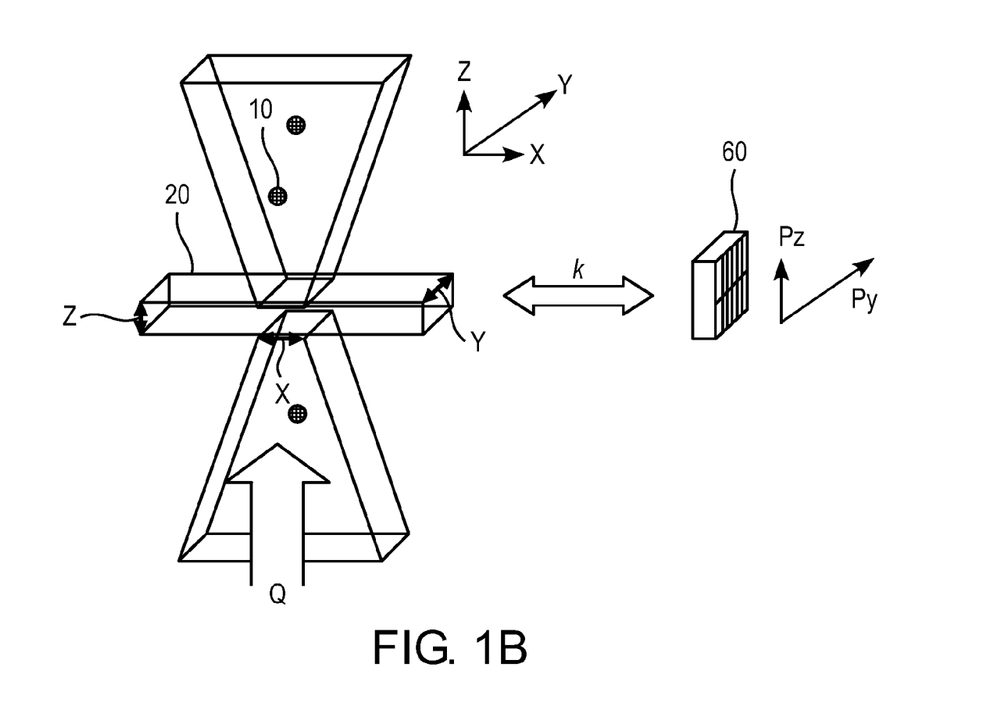
FIG. 1B shows an overview of the system and parameters for numerical estimations in an exemplary embodiment a particle monitoring system.

FIG. 1B shows an overview of an exemplary particle monitoring system and parameters for numerical estimations that will be discussed later.

Figure 1C:
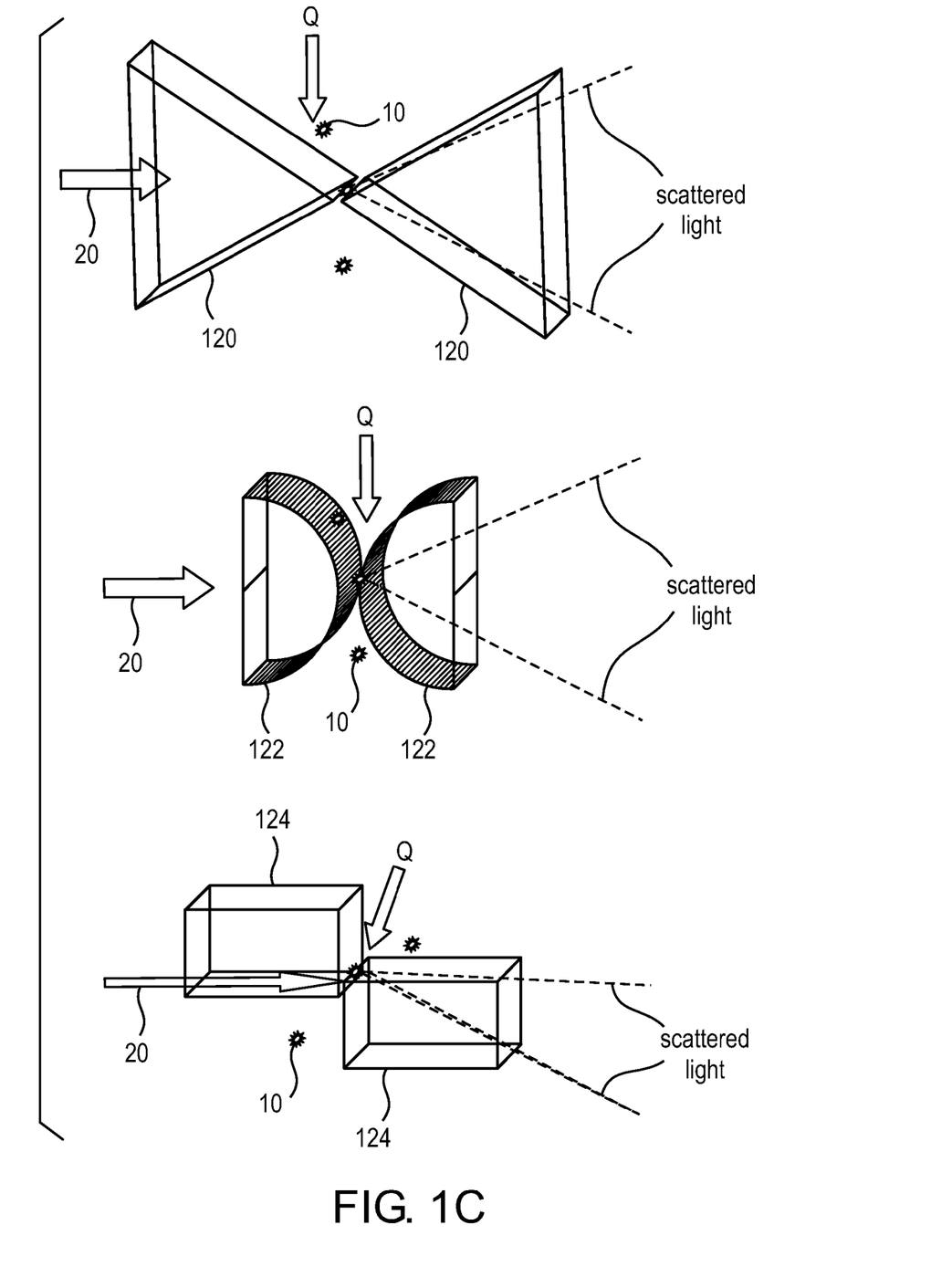
FIG. 1C shows an overview of examples of cuvettes according to a first embodiment (two optical elements with Y axis elongation and Z axis curvature)
Figure 1D:
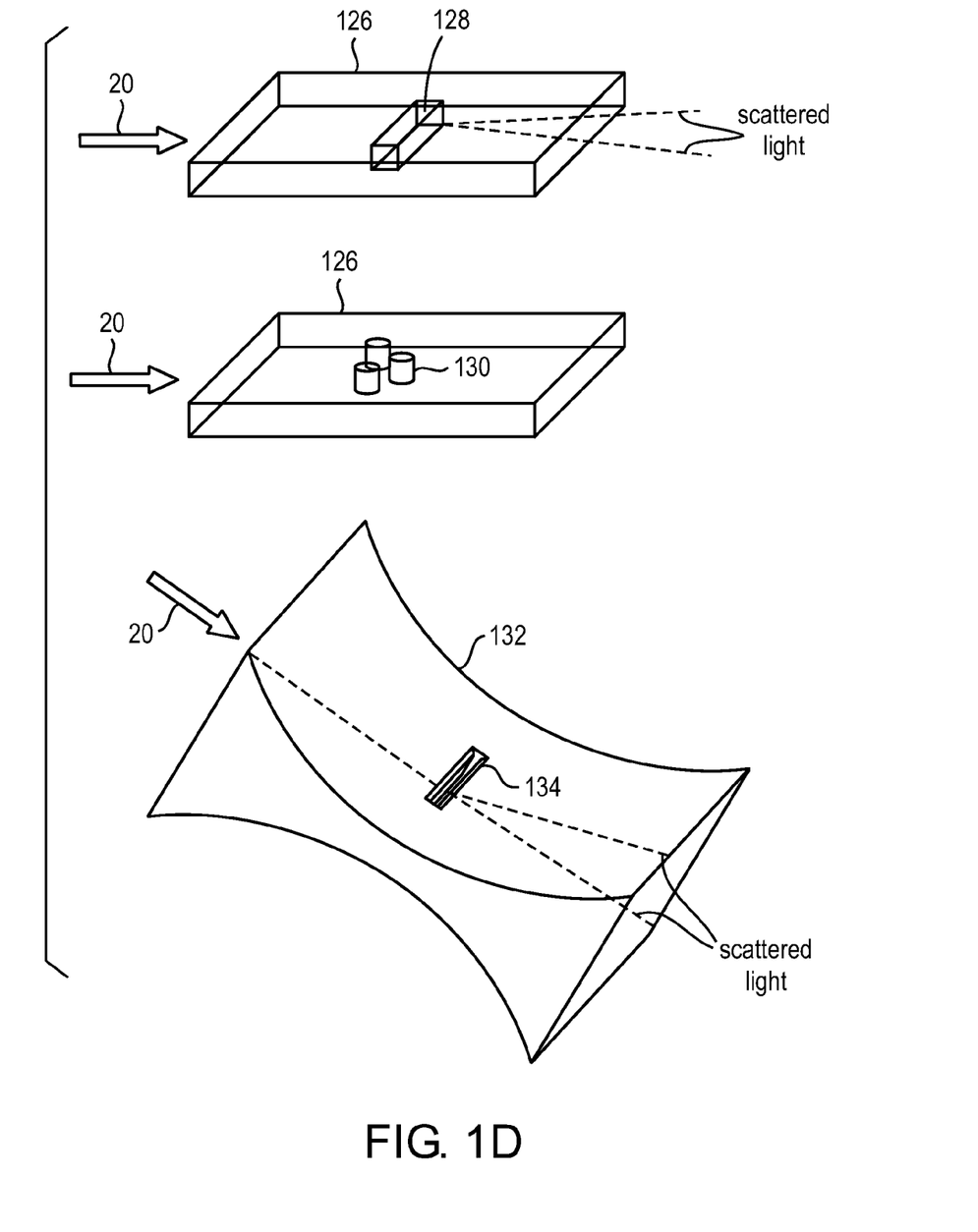
FIG. 1D shows an overview of examples of cuvettes according to a second embodiment (optical elements with flow passages elongated in the Y axis and confined in Z axis).

There can be several basic groupings into which exemplary designs for a particle monitoring system can be categorized. FIG. 1C shows an overview of examples of cuvettes according to a first group. Here, there can be two optical elements with Y axis elongation and Z axis curvature. Examples include two prisms 120 with opposing tips, two cylindrical lenses 122 and two optical blocks 124 with minimal overlap on the Z axis. FIG. 1D shows an overview of examples of cuvettes according to a second group. Here, there can be optical element 126 with flow passage 128 elongated in the Y axis and confined in Z axis. These designs may include, for example, a monolithic waveguide structure with a slit for flow that is limited in the Z direction. Another group of designs could include a combination of features. For example, one optical element could have substantial curvature in the Z direction and another element could include a flat section. Another embodiment could include a flat optical waveguide 126 with a set of holes 130 for sample flow. In this embodiment, the holes 130 may not overlap in the X direction. In another embodiment, there may be a biconcave cylindrical lens waveguide 132 with a slit 134 for sample flow.

The transparency of the sample flow can be arranged in a form that can be relatively thin in first (X) and second (Z) orthogonal dimensions and long in a third (Y) orthogonal dimension. Exemplary optimal sample thicknesses can be determined using, for example, two criteria. A first criterion can be based either on the absence of significant multiple scattering of light by the sample or the existence of relatively high sample transparency; this criterion can determine thickness in the first dimension.

A second criterion can be based on desired pressure drop of the optical cuvette at required flow rates. Pressure drop inside of an optical cuvette can be an important factor for method applicability in industry. There may be an acceptable range of pressure drops that can be introduced by a device (like in-line monitoring device) into flow lanes. This range can vary from application to application and depends from process parameters. Pressure drop inside of a cuvette can be a reverse function of flow thicknesses in the first and third dimensions and which can determine the cross section of the cuvette. Because the flow thickness in the first dimension X can be determined by optical transparency criterion and may not be varied freely, the flow width in third dimension Y can be used to keep the pressure drop at a desired level. The pressure drop can be directly proportional to the flow dimension in the second direction Z and this also can be used to affect the pressure drop in the cuvette in a desired manner.

In one example, a sample fluid flow having an X dimension (e.g., a thickness) in the range of approximately X=5 μm to 500 μm (e.g., a preferable range of 100 μm to 200 μm, in particular about 100 μm), a Z dimension in the range of Z=0.1 mm to 5 mm (e.g., a preferable range of 0.1 mm to 1.0 mm, in particular about 1.0 mm) and a Y dimension (e.g., a width) of Y=5 mm to 25 mm can be established. As referenced herein, and throughout the specification, the term "about" means, for example ±10%.

A diverging angle in the output part of cuvette can also affect pressure drop in the cuvette at a given flow rate and may be chosen accordingly. Another criterion to choose the diverging angle can be its affect on flow structure. For example, a high diverging angle (an extreme case is a right angle, i.e., slit in flat material) most likely generates turbulent motion in the flow. When turbulence is not desirable it can be prevented by choosing proper diverging angle of cuvette.

In exemplary embodiments, laser light extinction and multiple light scattering by the particles can be negligible. At the same time, the slurry flow may require no dilution and therefore the size distribution of the particles in the slurry can have minimum distortion.

Numerical Estimations

In one embodiment, referring again to FIG. 1B, flow parameters at a measuring point are width Y, thickness X, flowrate Q. A laser beam of Lp (not shown) power has width Y and thickness Z. A measuring area Z*Y is projected by an optical system with magnification k to a camera-type sensor 60 with Py*Pz pixels (pixel sizes are $z_p$ and $y_p$) and signal accumulation time $t_c$. Optical magnification is chosen for whole flow observation:

$$Y=k*Py*y_p.$$

Particle velocity in the measuring area is V=Q/(X*Y). Signal registration time is t=Z/V or $t=z_p/k/V$, which one is smaller. Assuming $t<t_c$ (valid for most cases) the signal amplitude is:

$$S=Lp*F(d)*X/Q*(z_p/k/Z),$$

where F(d) is light scattering function for particle of size d. For particles in scattering media, the detection limit is determined by signal/noise ratio rather by signal value itself. Signal/noise ratio can be affected by two parameters—the volume of scattering media illuminating the single pixel and ratio of signal and noise accumulation times. Multiplying these two factors for signal/noise ratio results in:

$$SN=Py/t_c/Q*(F(d)/F(d_m)),$$

where $d_m$ is median particle size in the scattering media. SN does not necessarily depend on flow spatial parameters. This allows varying flow thickness X to achieve flow transparency without affecting signal/noise ratio.

Multiple light scattering may be negligible for sample optical thicknesses below one (i.e., transmission>exp(−1)). The range of acceptable sample optical thickness can be extended up to five or more at small signal collection angles. In that case, the correction of the Beer-Lambert light scattering law can be modified.

The parameters of the sensor (e.g., detecting camera) can also be as important as the total flow rate. Some exemplary calculation results for two cameras (1024 and 2048 pixels) and two flow rates are shown in Table 1. Detectable particle size $d_p$ is estimated in assumption of Raleigh scattering (F(d) ~$d^6$) and signal to noise ratio of 1 (slurry parameters are d=100 nm and N=1e12 1/cc).

TABLE 1

| | | | | | |
|---|---|---|---|---|---|
| X | mm | 0.1 | 0.1 | 0.1 | 0.1 |
| Y | mm | 10 | 10 | 10 | 10 |
| Z | mm | 0.1 | 0.1 | 0.1 | 0.1 |
| Q | ml/min | 500 | 500 | 250 | 250 |
| Scan rate | Hz | 10000 | 29000 | 10000 | 29000 |
| Py | | 1024 | 2048 | 1024 | 2048 |
| SN (d = $d_m$) | | 1.23E−06 | 7.13E−06 | 2.46E−06 | 1.43E−05 |
| $d_p$ ($d_m$ = 100 nm) | mkm | 1.0 | 0.7 | 0.9 | 0.6 |

It can be seen from Table 1 that with simple assumptions individual particles as small as 600 nm to 1000 nm (or lesser or greater) can be detected. The detectable particle size can be reduced by, for example, operating at signal-to-noise (S/N) ratios below 1, which may be technically feasible.

FIGS. 2A, 2B, 2C and 2D show an exemplary particle monitoring system 200 according to a first embodiment. In this embodiment, particle monitoring system 200 comprises a cuvette 210, e.g., a transparent optical flow cell, configured to confine a flowable sample. The flowable sample may be opaque to at least a first range of wavelengths of light waves. A transparent flow compression element 220, e.g., prisms, can be located within the cuvette 210 and configured to compress the flowable sample in a first (X) direction while controlling the sample in a second direction (Z) parallel to the direction of flow and orthogonal to the first direction while elongating the sample in a third direction (Y) orthogonal to the first and second directions. When the sample is compressed in the first direction, it can become transparent to at least one of the wavelengths in the range of wavelengths of light waves.

In one embodiment, exemplary X, Z and Y dimensions can be about 50 μm to 3 mm in the first (X) direction (e.g., at or about 100 μm), about 10 μm to 3 mm in the second (Z) direction (e.g., at or about 100 μm), and about 5 mm to 25 mm in the third (Y) dimension (e.g., at or about 10 mm to 20 mm).

Figure 2A:
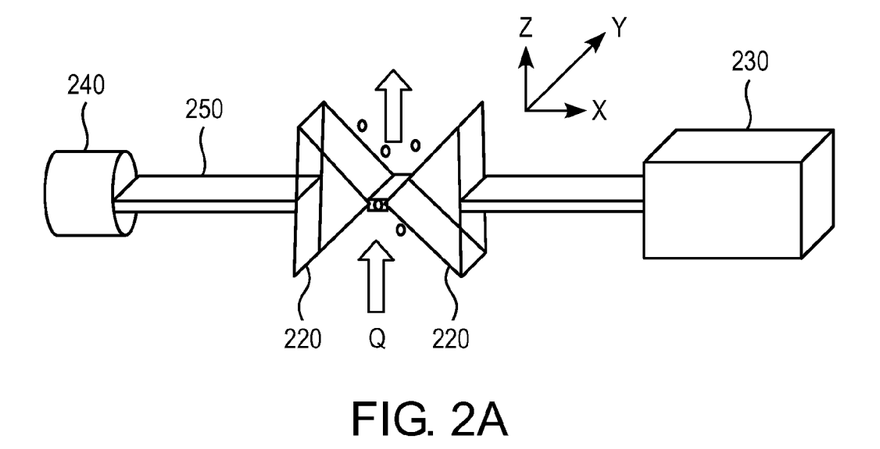
FIG. 2A shows an overview of an exemplary particle monitoring system according to a first embodiment.
Figure 2B:
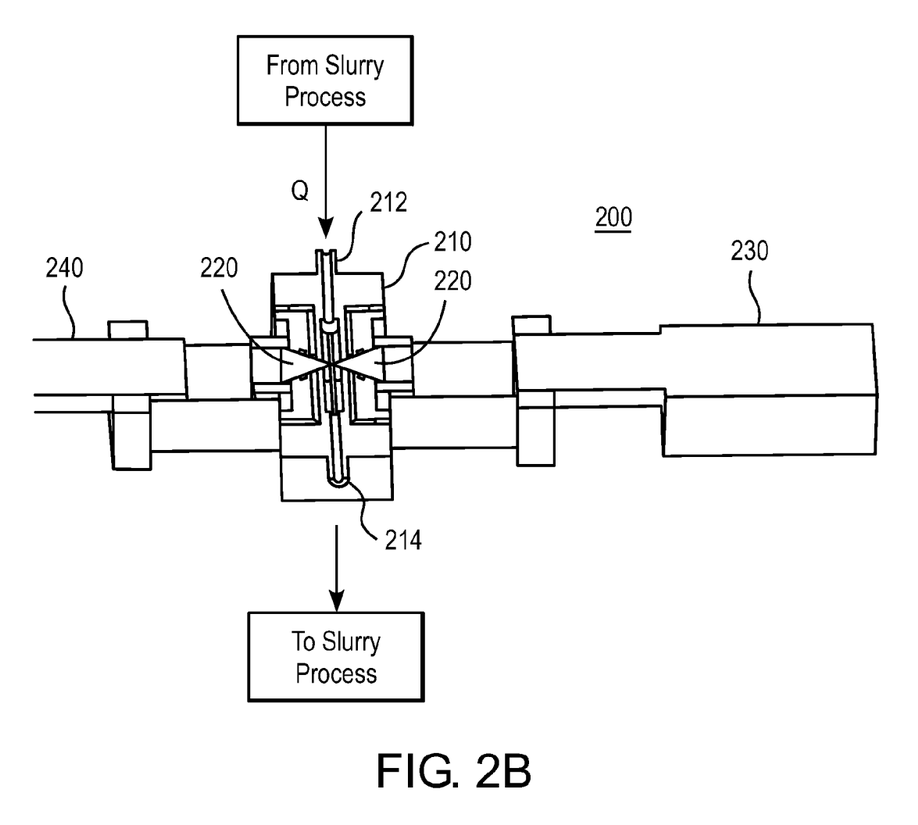
FIG. 2B shows a more detailed cross-sectional view of an exemplary particle monitoring system according to a first embodiment.

In one embodiment, an optical flow cell, such as a cuvette 210, can be used to form a focused flow of the sample fluid. The cuvette 210 can include a flow converging part, a measuring part, a sample introduction part 212 and a sample discharge part 214. The width of the flow channel in the measuring part of the cuvette 210 can be narrow in the first dimension (e.g., 0.1 mm±10% or lesser or greater) and wide in the third orthogonal dimension (for example, approximately 10 mm±10% or lesser or greater).

The effective flow dimension in the second orthogonal direction may be determined by the curvature of the flow focusing elements and can be in the range of, for example, 10 μm to 3 mm. The flow channel parameters can be substantially constant (e.g., ±10% flow channel width in any direction) along the whole length of this measuring part of the cuvette 210. The measuring part of the cuvette 210 can be optically transparent and may be used for characterization of the sample transparency and for the optical characterization of particles in the focused sample fluid.

Figure 2C:
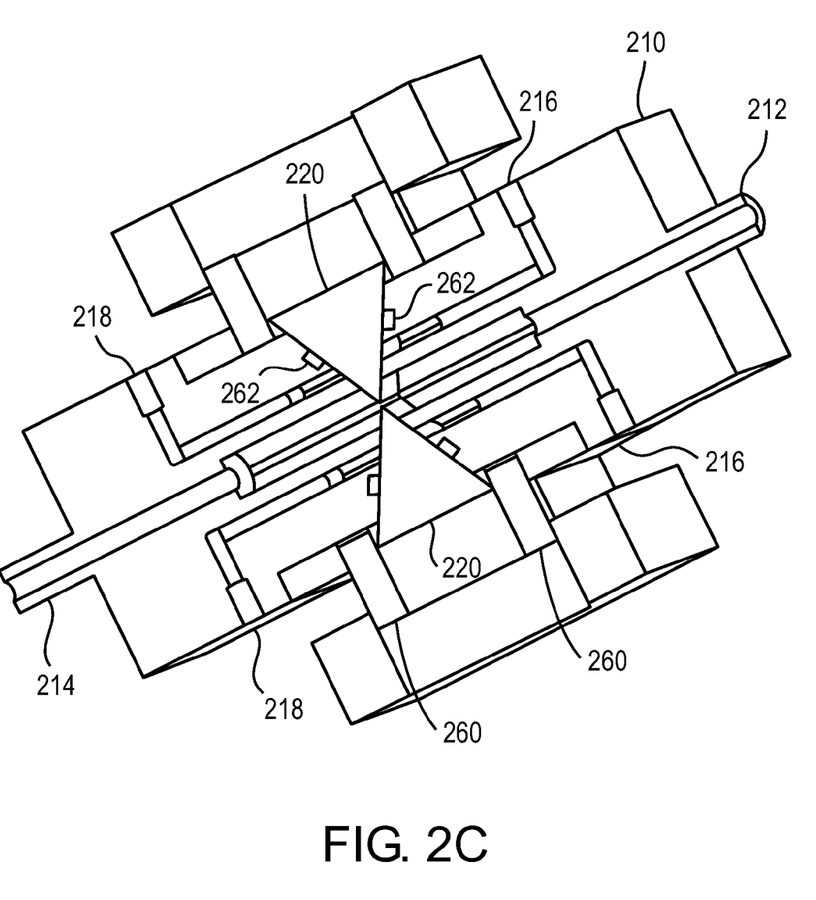
FIGS. 2C and 2D show a cross-sectional view of an exemplary particle monitoring system according to the first embodiment incorporating surrounding flow.
Figure 2D:
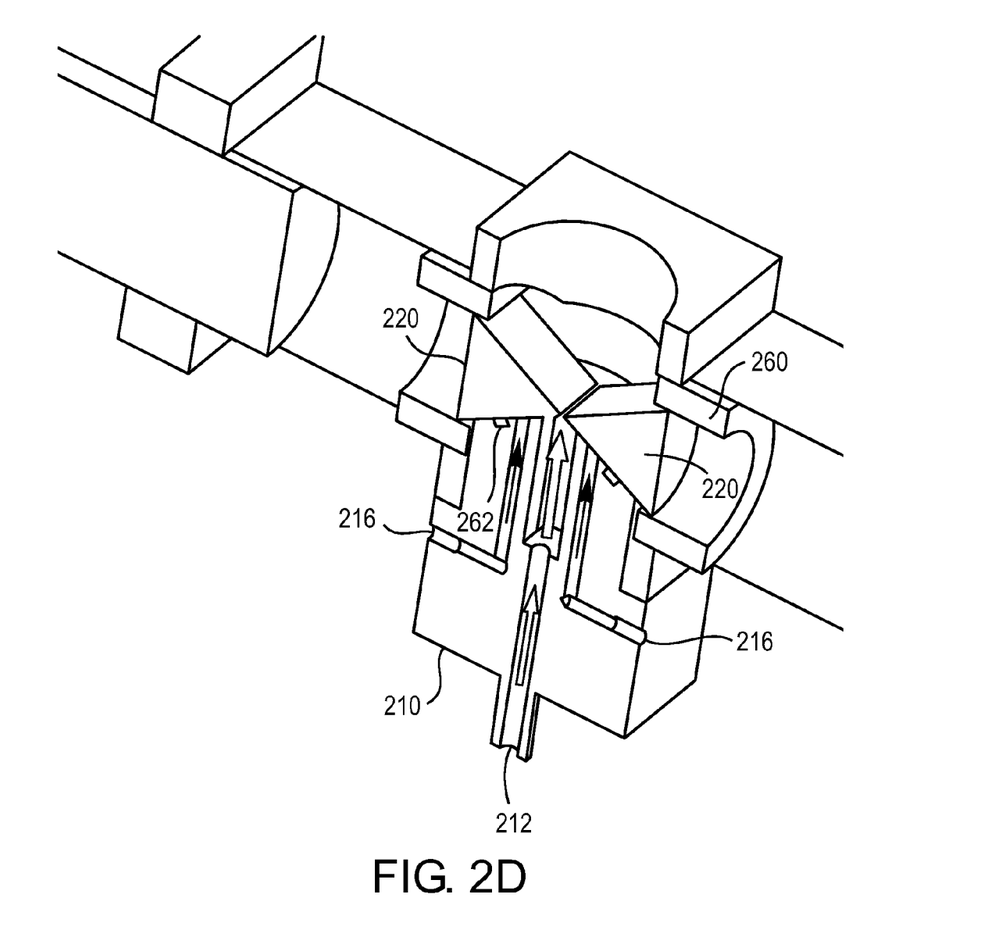

In one embodiment, as shown in FIGS. 2C and 2D, sample fluid flow can also be placed into operable communication (e.g., at least partially surrounded) with a flow of clean (i.e. relatively particle-free) transparent liquid (e.g., water) or other appropriate liquid. This may be accomplished by introducing and removing the clean transparent liquid via surrounding flow inlets 216 and outlets 218, for example. This method can be used to avoid the contamination of optical parts or as another method to control sample flow thickness and transparency. An exemplary optical cuvette having symmetrical surrounding flow inlets is illustrated in FIGS. 2C and 2D. Main sample flow can be introduced through the flow inlet 212 and discharged through the sensing area formed by the tips of the prisms 220. A surrounding flow of clean liquid compatible with sample liquid parameters can form a boundary layer on the prism 220 surfaces preventing particle deposition on optical surfaces. Surrounding flow can be chosen compatible with sample flow and flow rates can be minimal so as not to affect the sample flow properties.

In one embodiment, an exemplary way of compressing flow is represented in FIGS. 2A, 2B, 2C and 2D as two optical elements (e.g., prisms 220) having a gap formed between the tips, to compress the sample and render the sample transparent to at least one wavelength of light waves. The tips of the prisms 220 may be designed to provide the necessary optical quality. Prisms as flow forming optical elements can satisfy the parameters mentioned above: elongation by axis Y and short distance by axis Z. The optical signal can be collected through the flat surface of the prism opposing the sensing volume forming tip. The prism angle from tip to flat surface can be chosen depending on requirements of the signal detection system—for light transmission schemes the angle can be small, for light scattering schemes bigger angles can be used for scattered light collection.

Symmetrical or asymmetrical prisms can be used depending on requirements for converging and diverging angles of the flow. Those skilled in the art will appreciate that in any or all of the foregoing embodiments, as well as variations thereof, the cuvette can be configured using two optical elements, such as two equilateral (or other) prisms to produce a flow cell for compressing the sample in at least one dimension to render the sample transparent to light waves of a predetermined wavelength.

The system also can be configured to identify characteristics of individual particles contained in the compressed sample. In one embodiment, an identifying device is represented in FIG. 2B as an optical camera or detector 230 (e.g., a line scanner, a CCD camera, CMOS, photodiode or other optically sensitive device) in optical communication with the cuvette 210. An associated light source 240, e.g., a laser, which produces a beam of light 250, can also be in optical communication with the cuvette 210.

The sample transparency can be measured by light extinction, and the sample fluid thickness in the flat part of the cuvette 210 can be adjusted to obtain a predetermined transparency value or sensing volume value. Known light scattering and/or light extinction techniques can be used to measure the parameters of single particles having diameters above the detection limit. A CCD (charge-coupled device) or CMOS detector/camera 230, together with appropriate frame-capture electronics and data-handling software, can be used to suppress the influence of background scattering on the quantitative detection of the signal produced by individual particles passing through the optical sensing volume.

FIGS. 2C and 2D shows more details of an exemplary cuvette 210 according to a first embodiment. The cuvette 210 can include the body assembly for the parts, prisms 220 attached to actuators 260, and two symmetrical holders. Proper sealing in the holder-prism interface can be provided by o-rings (e.g., Kalrez or Chemrez material). To achieve a variation in the channel thickness, the cuvette 210 can be configured using two symmetrical optical parts, such as prisms 220, separated by, for example, an elastic spacer 262 formed of, for example, O-ring cord or any elastic material.

Prisms 220 (e.g., sapphire or glass, coated with diamond like carbon) can be attached to actuators 260 allowing the prism's displacement to adjust the sensing area width. Externally controlled pressure can be applied on these two opposing parts using, for example, screws, hydraulic or pneumatic actuators, electromagnetic actuators or any other way to control displacement to cause shrinkage in the spacer to a level that depends on the applied pressure and Young's modulus of elasticity for the spacer. This can allow control of the sample transparency, because the focused fluid sample thickness can have a known relationship (e.g., be proportional) to the flow channel thickness. Actuators 260 can also be used to provide high frequency (ultra- or megasonic) vibration of the prisms 220 to reduce possible particle deposition on optical parts.

Exemplary embodiments such as this can allow a measurement of the sample transparency as a function of sample thickness in a single experiment. These measurements can permit a determination of the particle size parameters in the sample fluid using an integral scattering approach. At the same time, the parameters of the largest particles can be determined using a single-particle approach. The combination of these two different approaches (that is, integral and differential) can permit an improvement in the accuracy and reliability of the measurements.

In one exemplary embodiment shown in FIG. 2B, the particle monitoring system can be part of a system for supplying a slurry to a process that utilizes the slurry. In this embodiment, the entire slurry utilized by the process can be monitored as the flowable sample. Thus, in one exemplary embodiment, such in-line monitoring can provide particle monitoring of up to 100% of the total flow within a process to be monitored.

Figure 3A:
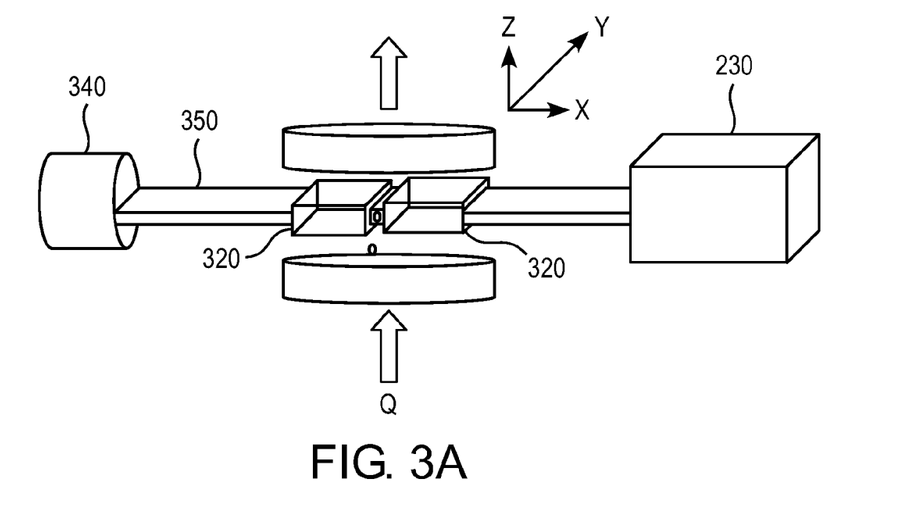
FIG. 3A shows an overview of an exemplary particle monitoring system according to a second embodiment.
Figure 3B:
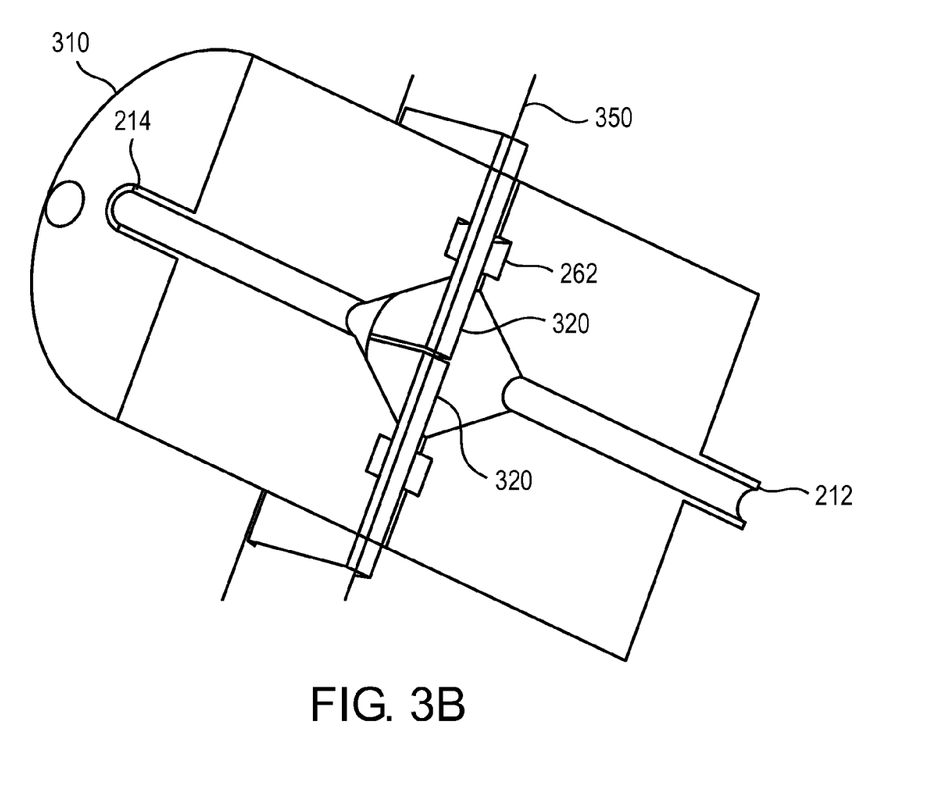
FIG. 3B shows a more detailed cross-sectional view of an exemplary particle monitoring system according to a second embodiment.

In a second embodiment, as shown in FIGS. 3A and 3B, the sample fluid flow can be introduced into a flat part of the cuvette 310, which can be formed by two flat optical waveguides 320. In a variation of this embodiment, a monolithic waveguide structure with a slit for flow that is limited in the Z direction from the second group of designs mentioned previously can be used. The second embodiment can allow for a simple mechanical design of a cuvette in several possible embodiments. However, optical measurements can be made in transmission mode and flow may have substantial recirculation (e.g., 50% or greater recirculation) after passage through measuring area.

The sample fluid in the flat part of the cuvette 310 can be illuminated with a light beam 350 of appropriate shape from a laser 340 or any other suitable light source. The beam shape can be chosen using criteria such as being wide enough to cover the whole flow width and narrow enough to go through optical waveguides 320. The intensity of the transmitted light can be measured and analyzed to determine the sample transparency. The width of the focused sample fluid flow can be adjusted to reach the desired level of sample transparency. When the desired level of sample transparency is achieved, the size parameters of the particles (for example, the particle size distribution above a given threshold diameter) in the sample fluid can be measured by known optical and electronic methods with relatively high accuracy.

Figure 4A:
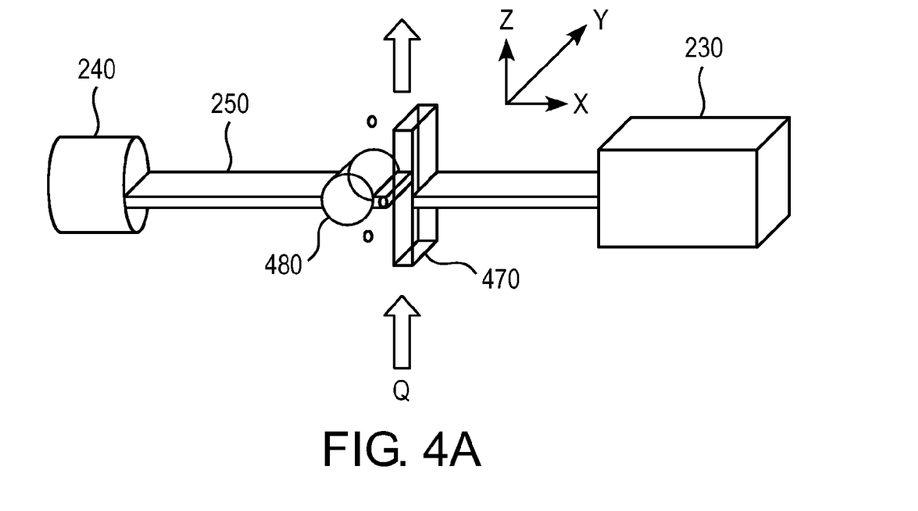
FIG. 4A shows an overview of an exemplary particle monitoring system according to a third embodiment.
Figure 4B:
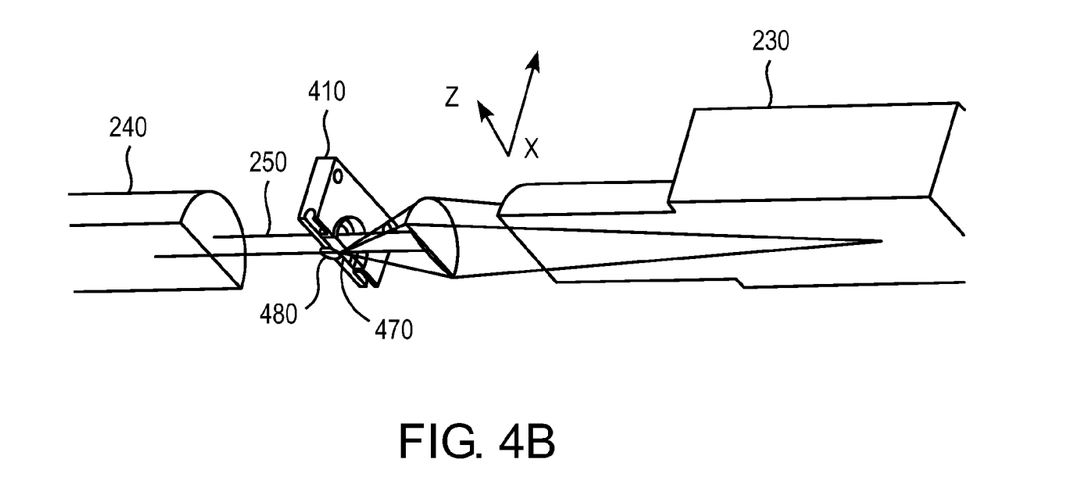
FIG. 4B shows a more detailed cross-sectional view of an exemplary particle monitoring system according to a third embodiment.
Figure 4C:
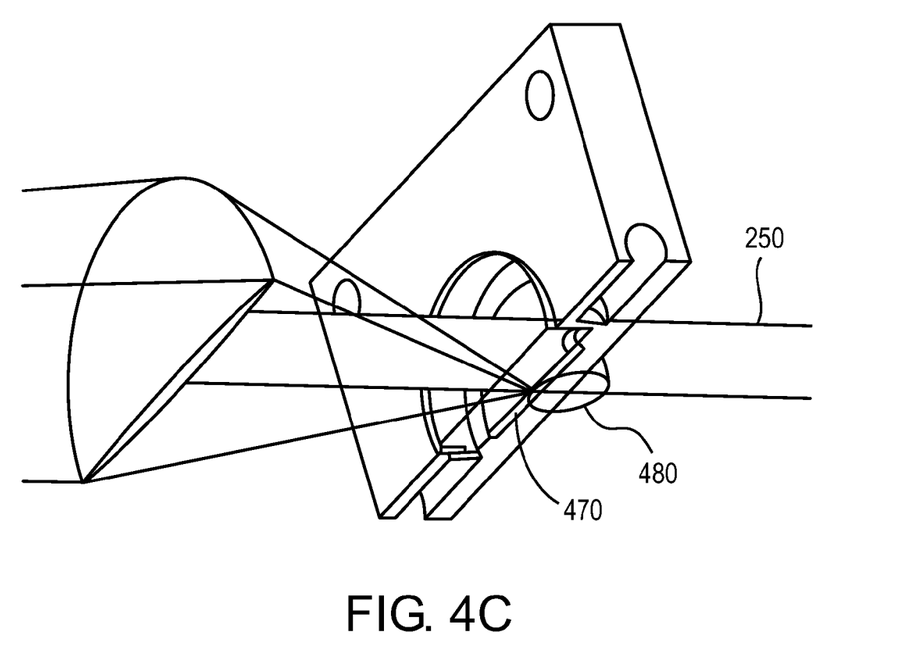
FIG. 4C shows a more detailed view of a cuvette in an exemplary particle monitoring system according to a third embodiment.

In a third embodiment, as shown in FIGS. 4A, 4B and 4C, the sample fluid flow can be introduced into the flat part of the cuvette 410 which can be formed by a flat optical window 470 and a cylindrical lens 480. This embodiment can allow a bigger optical signal collection angle but may have challenges in mechanical design of the cuvette 410. Dimension Z can be determined by lens diameter and may be substantially bigger than in the first or second embodiments.

Figure 5:
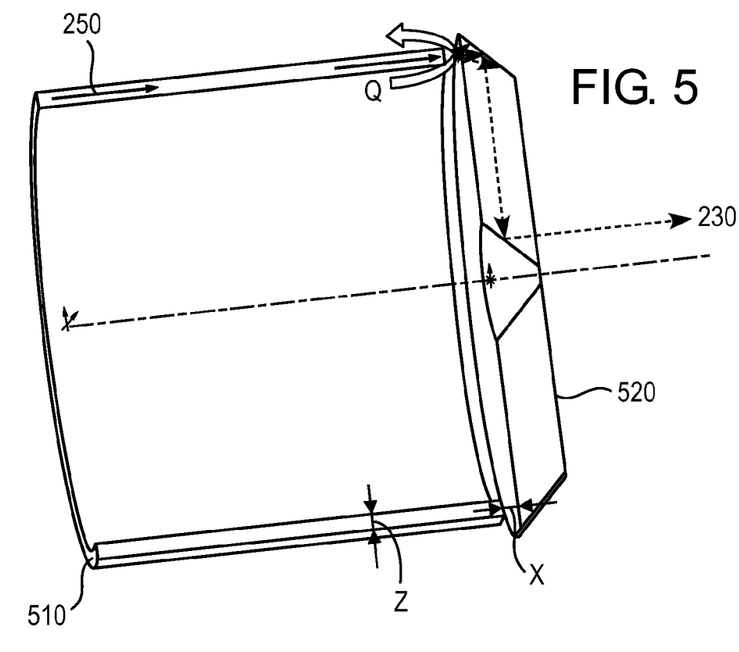
FIG. 5 shows a view of an exemplary optical cuvette according to a fourth embodiment.
Figure 6:
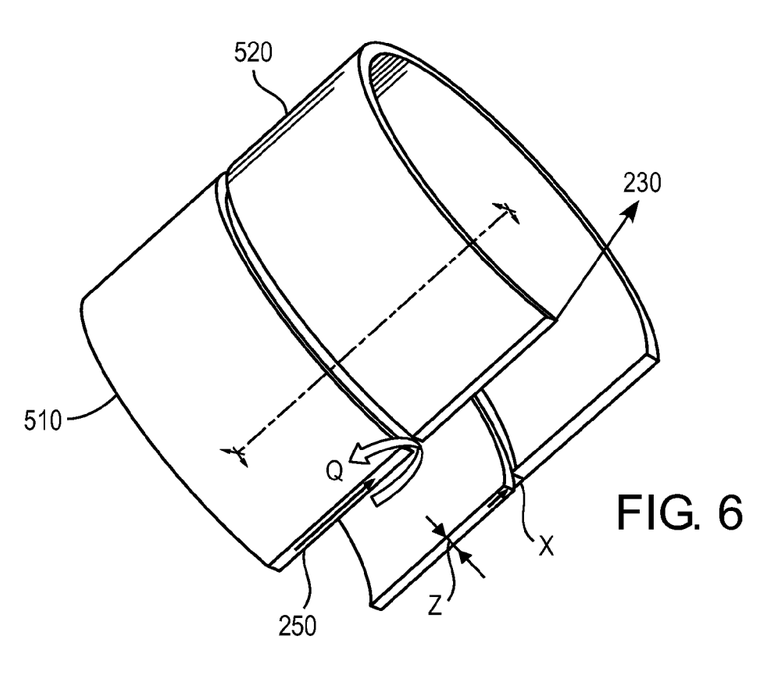
FIG. 6 shows a view of an exemplary optical cuvette according to a fifth embodiment.
Figure 7A:
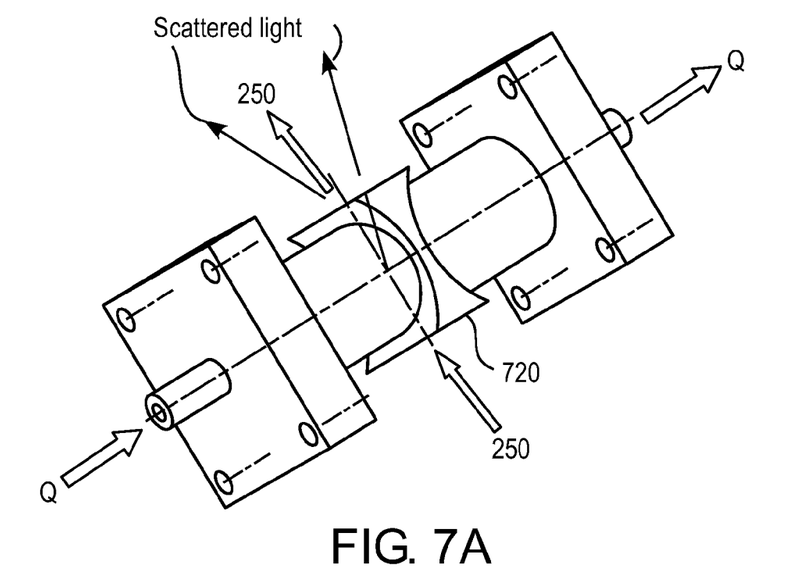
FIGS. 7A, 7B, 7C and 7D show views of an exemplary particle monitoring system according to a sixth embodiment employing a biconcave cylindrical lens as a waveguide.
Figure 7B:
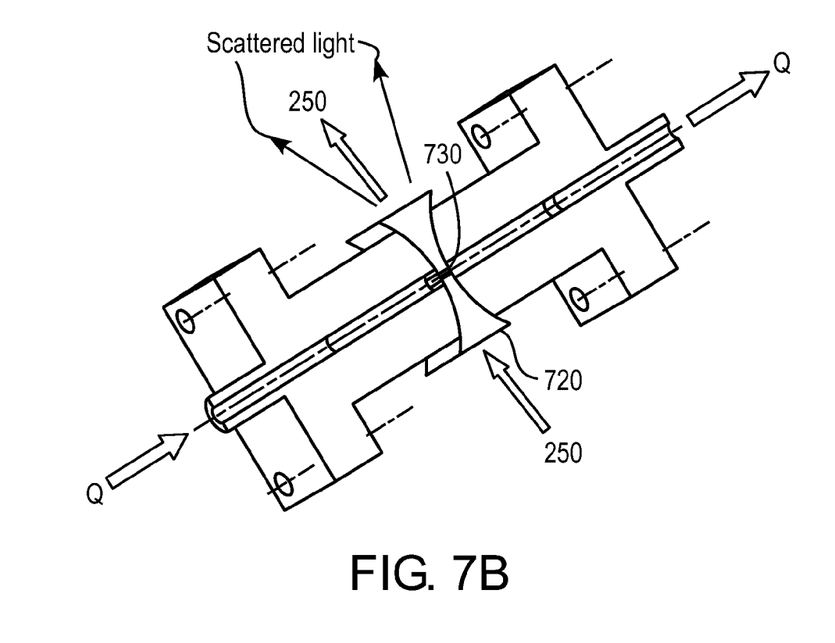
Figure 7C:
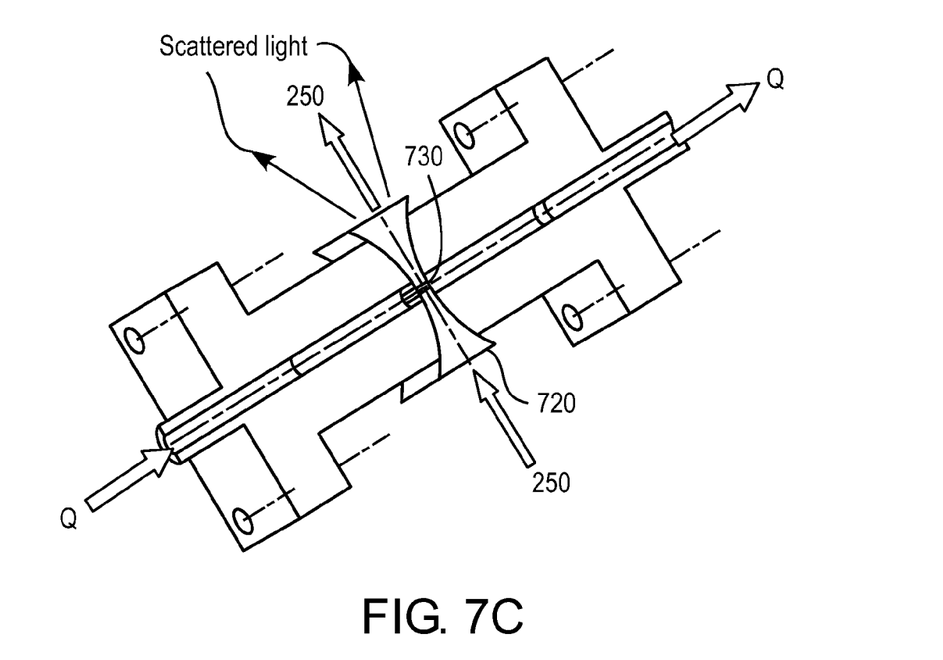
Figure 7D:
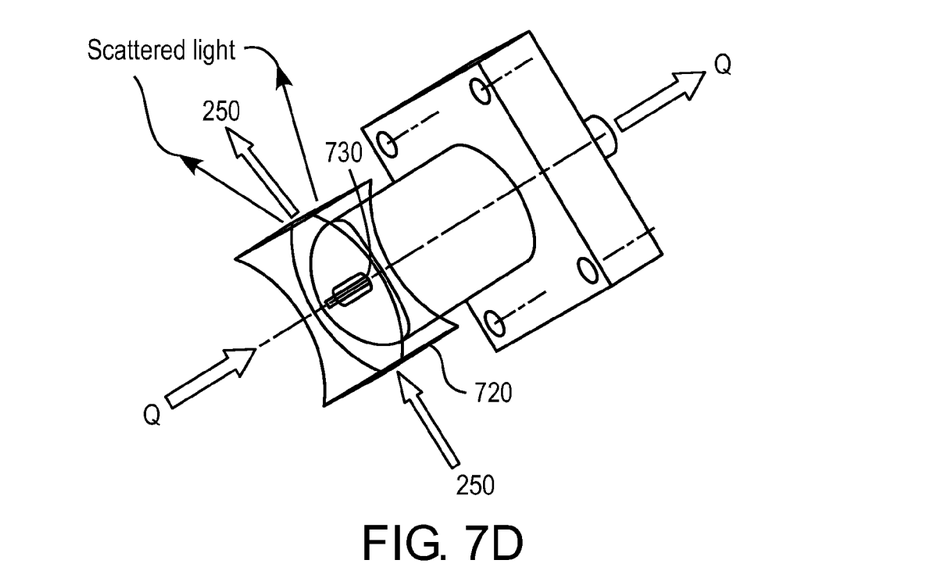

FIG. 5 shows an example of a fourth embodiment. As shown, the sample flow can be a circular "thread" of flow with thickness X. An exemplary light guide 510 and scattered light collection system 520 can be made of glass, sapphire or quartz. Scattered light can be delivered to a light detection and signal processing system by a fiber optic guide. This guide can be used to connect (convert) a circularly distributed signal with a linear optical detector. FIG. 6 shows a fifth embodiment similar to the fourth embodiment.

FIGS. 7A, 7B, 7C and 7D show views of an exemplary particle monitoring system according to a sixth embodiment. In this embodiment, a waveguide 720 can be formed using a biconcave cylindrical lens. A slit 730 can be cut in the middle of lens and polished for light passage. In this embodiment, the slit width can be fixed.

Experimental results suggest the feasibility of the concepts described herein. For example, experiments were performed with an optical cuvette of the third embodiment (i.e., formed by a flat window and a cylindrical lens). An example of this optical cuvette is shown in FIGS. 4A, 4B and 4C. In this exemplary embodiment, the width of flow was 10 mm and sample thickness (X, measured with a shim) was ~100 μm. The diameter of the cylindrical lens was 5 mm and the window diameter was 20 mm. The cylindrical lens was used to partially focus the laser beam in the cylinder-window vicinity (sensing area). The laser beam was widened before approaching the optical cuvette by another cylindrical lens to provide uniform irradiation along whole sample length in the Y axis.

In this exemplary experimental embodiment, the housing was made of black Delrin material and the windows were partially glued or rubber-tight sealed. The measured pressure drop at these cell parameters was ~1.5 psi for a flowrate of 100 ml/min. This pressure, which translates to 7.5 psi at 500 ml/min, should be acceptable, for example, for most semiconductor applications.

In this embodiment, the sample was irradiated with a laser to which custom modifications were made to reduce pulse length to eliminate the image "smearing" of moving particles. The laser beam was stopped at the collection lens plane and a collection lens was used to direct forward scattering light to a video camera (WT-502 by Watec Corp.). The images were recorded on a PC with Airlink+ frame grabber.

In this embodiment, the experimental results showed that non-diluted slurry looks like "milky" uniformly scattering media. Because of the small thickness the slurry was transparent for the illuminating wavelength(s) used. 1588 nm polymer microspheres from Duke Scientific Corp. in DI water were used to test for optical system sensitivity and the ability to record particles of such size. The same concentration of 1588 nm microspheres was also placed in a slurry. The results showed that the added particles are clearly detectable in DIW as well as in slurry.

In this embodiment, the experimental data suggests that:
1. Slurry becomes transparent at a certain thickness and optical methods can be applied for particle characterization.
2. The cuvette resistance to flow can be kept low to facilitate the operation at relatively high flow rates, e.g., 500 ml/min or greater.
3. The entire in-line flow to be supplied to a process that utilizes the slurry can be irradiated and monitored (i.e., surveyed) (e.g., for the presence of particles which exceed a specified (e.g., empirically determined threshold that has been set as a function of, for example, particle diameter in at least one dimension).
4. Background scattering from slurry does not prevent the registration of big particles which exceed the specified threshold.

Thus, in one embodiment, experimental results suggest that 100% of the slurry "flow" (i.e., the entire flow can be monitored (e.g., in-line) at flowrates up to, for example, 500 ml/min or greater. That is, a total flow that is to be used for in-line processing can be monitored, as opposed to a fractional flow which has been bled off of the process flow (i.e., directed from the main flow) as a representative sample for monitoring purposes).

As described, exemplary embodiments are directed to non-intrusive systems and methods for in-situ and/or in-line or off-line monitoring of single particles over a wide range of sizes and concentrations, contained in systems comprised mostly of smaller particles. Exemplary methods can accommodate mixtures without requiring their dilution, and mixtures wherein the "tail" of largest particles in the particle size distribution can be accurately measured. Optical characterization of particles over a wide range of sizes and concentrations in concentrated systems may be achieved using exemplary embodiments of an optical flow cell, such as a cuvette, wherein the sample flow is made relatively transparent to apply an optical technique for particle characterization.

The above description is presented to enable a person skilled in the art to make and use the systems and methods described herein, and it is provided in the context of a particular application and its requirements. Various modifications to the embodiments will be readily apparent to those skilled in the art, and the generic principles defined herein may be applied to other embodiments and applications without departing from the spirit and scope of the claims. Thus, there is no intention to be limited to the embodiments shown, but rather to be accorded the widest scope consistent with the principles and features disclosed herein.

What is claimed is:

1. A particle monitoring system, comprising:
   a cuvette configured to confine a flowable sample, the flowable sample being opaque to at least a first range of wavelengths of light waves;
   a transparent flow compression element located within the cuvette and configured to compress the flowable sample in a first direction while controlling the sample in a second direction parallel to the direction of flow and orthogonal to the first direction while elongating the sample in a third direction orthogonal to the first and second directions, wherein when the sample is compressed in the first direction it becomes transparent to at least one of the wavelengths in the range of wavelengths of light waves; and a monitor for monitoring the flowable sample using the at least one wavelength.

2. The system of claim 1, wherein the transparent flow compression element comprises:

one or more optical elements.

3. The system of claim 2, wherein the one or more optical elements comprise:

two prisms.

4. The system of claim 2, wherein the one or more optical elements comprise:

two waveguides.

5. The system of claim 2, wherein the one or more optical elements comprise:

a cylindrical lens and an optical window.

6. The system of claim 2, wherein the one or more optical elements comprise:

a first light guide and a second light guide, wherein the second light guide is configured to deliver scattered light.

7. The system of claim 2, wherein the one or more optical elements comprise:

an optical waveguide configured with a hole through which the flowable sample flows.

8. The system of claim 2, wherein the one or more optical elements comprise:

a protective coating.

9. The system of claim 2, comprising:

a mechanism operatively connected to the one or more optical elements and configured to adjust a distance between the one or more optical elements.

10. The system of claim 9, wherein the mechanism comprises at least one of:

a screw, a hydraulic actuator, a pneumatic actuator, and an electromagnetic actuator.

11. The mechanism of claim 9, wherein the mechanism is configured to vibrate the one or more optical elements.

12. The system of claim 1, comprising:

a light source in optical communication with the cuvette.

13. The system of claim 12, wherein the light source comprises a laser.

14. The system of claim 1, the monitor comprising:

a detector in optical communication with the cuvette.

15. The system of claim 14, wherein the detector comprises:

at least one of a line scanner, a CCD camera, a CMOS camera, and a photodiode camera.

16. A method of particle monitoring, comprising:

confining a flowable sample, the flowable sample being opaque to at least a first range of wavelengths of light waves;

measuring transparency of the flowable sample;

compressing the flowable sample in a first direction while confining the sample in a second direction parallel to a flow direction of the flowable sample and orthogonal to the first direction, while elongating the sample in a third direction orthogonal to the first and second directions, wherein when the sample is compressed in the first direction, the sample becomes transparent to at least one of the wavelengths in the first range of wavelengths; and identifying characteristics of particles contained in the sample that has been compressed.

17. The method of claim 16, wherein the compressing comprises:

compressing to about 50 μm to 3 mm in the first direction while confining the flowable sample for about 10 μm to 3 mm in the second direction and elongating the flowable sample to about 5 mm to 25 mm in the third dimension.

18. The method of claim 16, wherein compressing comprises:

using a transparent flow compression element.

19. The method of claim 18, wherein the transparent flow compression element comprises:

one or more optical elements.

20. The method of claim 19, comprising:

adjusting a distance between the one or more optical elements using a mechanism operatively connected to the one or more optical elements.

21. The method of claim 20, wherein the mechanism is configured to vibrate the one or more optical elements.

22. The method of claim 16, wherein measuring transparency comprises:

irradiating the sample with a light source in optical communication with a cuvette used for confining the flowable sample.

23. The method of claim 22, wherein identifying characteristics of particles comprises:

detecting an optical signal using a detector in optical communication with the cuvette.

24. The method of claim 23, wherein the optical signal is transmitted through the sample.

25. The method of claim 23, wherein the optical signal is reflected from the sample.

26. The method of claim 16, comprising:

supplying a slurry to a process that utilizes the slurry, wherein the entire slurry utilized by the process is monitored as the flowable sample.

* * * * *